United States Patent
Schaeffer et al.

(10) Patent No.: US 7,618,824 B2
(45) Date of Patent: Nov. 17, 2009

(54) METHOD FOR EVALUATING THE ACIDITY OF OIL SAMPLES BY ISOTOPIC LABELLING

(75) Inventors: Philippe Schaeffer, Ernolsheim/Bruche (FR); Pierre Albrecht, Strasbourg (FR); Nicolas Rouquette, Le Havre (FR); Isabelle Kowalewski, Bailly (FR); Anne Fafet, Carrières-sur-Seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 436 days.

(21) Appl. No.: 11/443,223

(22) Filed: May 31, 2006

(65) Prior Publication Data

US 2007/0026524 A1 Feb. 1, 2007

(30) Foreign Application Priority Data

Jun. 2, 2005 (FR) .................................. 05 05683

(51) Int. Cl.
*G01N 33/03* (2006.01)
(52) U.S. Cl. .......................................... 436/57; 436/60
(58) Field of Classification Search .................. 436/57, 436/60

See application file for complete search history.

(56) References Cited

U.S. PATENT DOCUMENTS

| 4,755,469 | A | 7/1988 | Showalter et al. |
| 6,098,423 | A | 8/2000 | Leblond et al. |
| 2002/0086434 | A1 | 7/2002 | Roussis et al. |

FOREIGN PATENT DOCUMENTS

EP 0306333 3/1989

OTHER PUBLICATIONS

Meredith et al., Influence of biodegradation on crude oil acidity and carboxylic acid composition, Organic Geochemistry, 2000, 31, 1059-1073.*
Xiong et al., Carbon isotopic composition of individual n-alkanes in asphaltene pyrolysates of biodegraded crude oils from the Liaohe Basin, China, Organic Geochemistry, 2000, 31, 1441-1449.*
Head et al., Biological activity in the deep subsurface and the origin of heavy oil, Nature, Nov. 20, 2003, vol. 426, 344-352.*
Franks et al., Carbon isotopic composition of organic acids in oil fields waters, San Joaquin Basin, California, USA, Geochimica et Cosmochimica Acta, 2001, vol. 65, No. 8, 1301-1310.*

* cited by examiner

*Primary Examiner*—Walter D Griffin
*Assistant Examiner*—Christine T Mui
(74) *Attorney, Agent, or Firm*—Antonelli, Terry, Stout & Kraus, LLP.

(57) ABSTRACT

A method for evaluating the acidity of oil samples in small amounts, applicable at any stage of the petroleum industry, includes labelling by an isotope of a chemical element present in at least one acid function present in petroleum samples. Isotopic enrichment of the samples is then determined by isotope ratio mass spectrometry (IRMS). The acidity of the samples is deduced therefrom. This method is an alternative to the measurement of the Total Acid Number (TAN). In particular, it represents the only possibility to reliably measure the acidity of oil samples available in small amounts. The method can be applied to the economic evaluation of a hydrocarbon production field, to the determination of the carbon range responsible for the acidity of a crude, or to monitoring of the evolution of the acid distribution of a site polluted by hydrocarbons.

13 Claims, 2 Drawing Sheets

METHOD FOR EVALUATING THE ACIDITY OF OIL SAMPLES BY ISOTOPIC LABELLING

FIELD OF THE INVENTION

The present invention relates to a method for evaluating the acidity of an oil.

In particular, the invention can apply to any oil sample, even in small amounts (crudes, extracts, cuts, oil fractions, ... ), from any stage of the petroleum industry: Exploration/Production/Refining/Environment.

Since 90% of the world energy consumption will still be supplied by fossil fuels during the next decades, the petroleum industry will have to produce more and more difficult oils, in particular heavy oils. These heavy oils mainly result from the microbial alteration of conventional oils, a fundamental phenomenon at the origin of acid oils. It therefore is an important medium or long term pole of reserves renewal, provided that the technical, economic and environmental problems encountered for producing them can be solved. In fact, these biodegraded heavy crudes are characterized by a high acidity (TAN>0.5), in addition to very high proportions of heavy metals, sulfur and nitrogen, proportions that are much higher than those of conventional oils. These oils consequently require specific methods for producing, transporting and treating them.

The present invention is of great significance since it will allow to evaluate the acidity of crudes on small amounts during production and/or transportation at an early stage of characterization of an underground formation and of its development. It will also allow to selectively label the molecules responsible for this acidity in an oil sample (crude or extract) so as to best identify them, then to apprehend their physico-chemical properties.

BACKGROUND OF THE INVENTION

The following documents, mentioned in the course of the description hereafter, illustrate the state of the art:

Designation ASTM D664-95: American Standard Test Method for Acid Number of Petroleum Products by Potentiometric Titration, Annual Book of ASTM Standards, vol. 05.01, p. 250-256, Babaian-Kibala, E., Petersen, P. R., Humphries, M. J., 1998. Corrosion by naphthenic acids in crude oils. Pre-prints of the A.C.S., Division of Petroleum Chemistry vol. 3, 106-110, Meredith, W., Kelland, S.-J., Jones, D. M., 2000. Influence of biodegradation on crude oil acidity and carboxylic acid composition. Org. Geochem. 31, 1059-1073, Robbins, W. K., 1998, Challenges in the characterization of naphthenic acids in petroleum, 215th ACS Nat. Mtg. Dallas, preprints 43 (1), 137-140, Luo, Liwen, Xia, Daohong, 2003. Total carboxylic acids contents in petroleum reservoir rock determined by chemical titration. Prepr.—Am. Chem. Soc., Div. Pet. Chem. (Preprints—American Chemical Society, Division of Petroleum Chemistry) 48, 261-263, Roussis s g, Lawlor l j, 2002. Direct determination of acid distributions in crudes and crude fractions. Patent assignee: Exxonmobil res & eng co world 02/48698a1, p Jun. 20, 2002, f Nov. 6, 2001, pr us Dec. 14, 2000 (appl 60/255659) and us Sep. 21, 2001 (appl 957941) (g01n-024/00).

The acidity of an oil is generally defined in the petroleum industry from the number of milligrams of alcoholic potash (KOH) necessary to neutralize one gram of oil. This number is referred to as TAN (Total Acid Number). This TAN is obtained by potentiometric titration in a non-aqueous medium. This titration is carried out according to the standard ASTM method D664-95 described in the following document:

American Standard Test Method for Acid Number of Petroleum Products by Potentiometric Titration, Annual Book of ASTM Standards, vol. 05.01, p. 250-256.

This potentiometric method has the drawback of requiring a great volume of crude and consequently a large amount of samples (Table 1). In fact, this method is based on the measurement of an electric potential difference (expressed in mV) between a crude oil diluted in a solvent (toluene/propanol-2) before and after neutralization referenced in relation to a freshly prepared anhydrous acid buffer solution. The measurement depends on the sensitivity of the electrodes intended to measure very slight variations (millivolt scale). This is the reason why this measurement requires large amounts of oil; the lower the acidity, the larger the amounts (Table 1). Furthermore, it is essential to first eliminate any solid particle from the oil sample prior to applying this standard method. Calculation is carried out according to the following formula:

$$\text{TAN} = \frac{m_{KOH}(\text{mg})}{m_e(\text{g})} = (A - B) \cdot M \cdot \frac{56.1}{m_e(\text{g})}$$

with:
- $m_e(\text{g})$: mass of the oil sample in g,
- $m_{KOH}(\text{mg})$: mass of alcoholic potash (KOH) required to neutralize the mass of oil sample $m_e(\text{g})$,
- B: volume in ml of KOH required for titration of the solvent in the absence of oil (blank test),
- M: concentration of the KOH solution in mole/l,
- A: volume in ml of the KOH solution (0.1 mole/l) required for titration of the oil diluted in a solvent, until a turning point measurement as close as possible to the one obtained for the buffer solution is reached.

NB: molar mass of KOH=15.9994+1.00797+39.103=56.1.

TABLE 1

Amount of oil required to determine the acidity thereof according to standard D664-95

| TAN | Mass of sample required (g) | Weighing accuracy (g) |
|---|---|---|
| 0.05-1.0 | 20.0 ± 2.0 | 0.1 |
| 1.0-1.5 | 5.0 ± 0.5 | 0.02 |
| 5-20 | 1.0 ± 0.1 | 0.005 |
| 20-100 | 0.25 ± 0.02 | 0.001 |
| 100-250 | 0.1 ± 0.01 | 0.0005 |

An oil is considered to be acid if its TAN is above 0.5 mg KOH per gram of oil. From natural observations, the TAN scale of crudes ranges from 0.1 to 8 mg KOH/g oil (Babaian-Kibala et al., 1998; Robbins et al., 1998; Meredith et al., 2000). Although a TAN value of 0.5 is low, and the acid compounds remain minor constituents in crude oils, their role can be significant in terms of profitability during development of an oil field (reservoir quality uncertainty, low economic value of the crude, ... ). These acids are, among other things, responsible for emulsion, foaming and soap deposition (during production), corrosion (during production, transportation and/or refining) and environmental (waste water treatment, site pollution) problems. This global acidity measurement is to date the only one that is used and recognized by oilmen.

Various known methods concerning measurement of the acidity of crudes and/or characterization of the acids in production oils are for example described in the following publications:

Liwen, 2003, describes a back titration method (with excess potash) on crushed cores tested according to different parameters: grain size, extraction time, solvent volume (acetic acid/alcohol), . . . . The acidity measurements (in mmoles/g core) are higher than those obtained with the standard method and optimum conditions are described, Roussis describes another method intended for direct determination of the acid distribution in crudes or crude fractions by mass spectrometry in negative chemical ionization mode (Cl⁻). The chloride anions generated by CI react with the acid compounds of the oil samples. The chlorinated adduct ions are detected selectively and the acid species are quantified from the identified peaks.

Furthermore, the various methods currently proposed have integrated no relation with the TAN value measured according to the ASTM standard D664 and are therefore not used by the petroleum industry. Besides, these analyses are performed at a late production stage, from stock-tank or test oils.

The method according to the invention leads to the evaluation of the acidity translated in terms of isotopic enrichment of oil samples, even in small amounts. The method is furthermore applicable at any stage of the petroleum industry (Exploration/Production/Refining/Environment).

SUMMARY OF THE INVENTION

The invention relates to a method for evaluating the acidity of an oil sample. It comprises the following stages:

carrying out isotopic enrichment of at least one acid function present in said sample, determining the value of said isotopic enrichment of said sample, deducing the acidity of said sample from said enrichment values.

According to the method, said isotopic enrichment can be carried out from one of the heavy isotopes as follows: $^{13}C$, $^{18}O$, D.

Enrichment can comprise conversion of the carboxylic acid functions to methyl esters by means of a $^{13}C$-labelled methylation reagent.

Determination of the isotopic enrichment value can comprise the following stages:

measuring the isotopy of said chemical element of said sample prior to enrichment, measuring the isotopy of said chemical element of said sample after enrichment.

The isotopy measurements can be performed by isotope ratio mass spectrometry.

According to the invention, the evolution of the biodegradation of a polluted site can be evaluated from the following stages:

extracting from said site rock samples containing organic matter, extracting the organic matter from the mineral matrix, measuring acidity values $A_h$ of the organic matter from an isotopic enrichment, evaluating the evolution of the biodegradation of a polluted site from acidity $A_h$.

According to the invention, oil production and transportation conditions can be optimized from the following stages:

extracting from said site rock samples containing organic matter, extracting the organic matter from the mineral matrix, measuring acidity values $A_h$ of the organic matter from an isotopic enrichment, optimizing the oil production and transportation conditions.

According to the invention, molecules responsible for the acidity can be located and characterized by applying the following stages to oil extracts, subfractions or cuts:

measuring acidity values $A_h$ of said extracts, subfractions or cuts from an isotopic enrichment, deducing from said acidity values $A_h$, for each extract, subfraction or cut, the location and the characterization of the molecules responsible for the acidity.

The oil sample subfractions can be obtained by thin-layer or liquid chromatography from the sample and the oil sample cuts can be obtained by distillation.

According to the invention, a TAN value can be estimated from the following stages:

measuring TAN values of core extracts, measuring acidity values $A_h$ of said core extracts from said isotopic enrichment values, determining a law allowing to relate said TAN values to said acidity values $A_h$ from an isotopic enrichment, estimating a TAN value from said law and from all the acidity value measurements $A_h$ from an isotopic enrichment.

Finally, according to the invention, a TAN value can be estimated from a chart constructed from acidity values $A_h$ from an isotopic enrichment.

BRIEF DESCRIPTION OF THE FIGURES

Other features and advantages of the method according to the invention will be clear from reading the description hereafter, with reference to the accompanying figures wherein.

DETAILED DESCRIPTION

Figure 1:
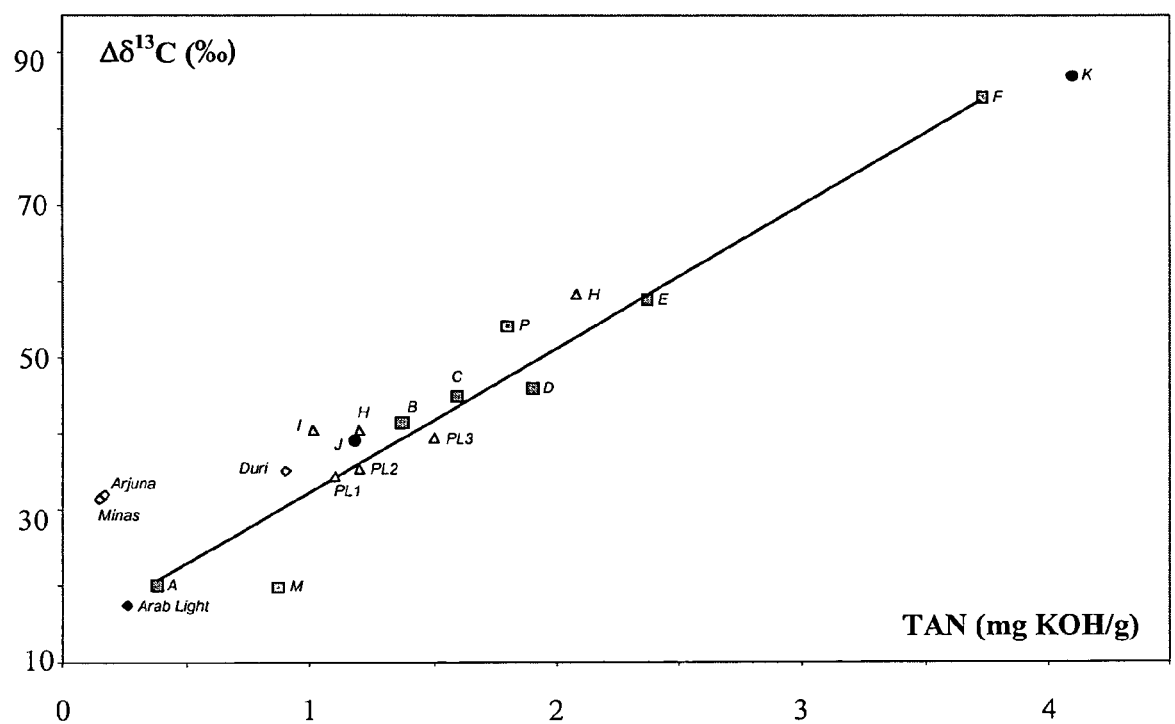
FIG. 1 illustrates the relation between the measurement performed $\Delta\delta^{13}C$ ($A_h$) and the TAN value obtained according to the ASTM standard D664, determined from crude oils of various geographic origins and characterized by various physico-chemical properties.

The principle of the method according to the invention for evaluating the acidity of oil samples, even available in small amounts, comprises isotopic labelling of the acid functions of these samples. It can be applied at any stage of the petroleum industry (Exploration/Production/Refining/Environment).

The method can then be broken up into three main stages:

1—carrying out isotopic labelling of the acid functions of an oil sample,

2—measuring the isotopic enrichment of the labelled and non-labelled oil sample, 3—deducing the acidity of the oil.

1—Isotopic Labelling of the Acid Functions

The compounds responsible for acidity that can be present in a petroleum fluid are numerous and they mainly come in two forms. The following examples can be mentioned:

acid gases: $H_2S$ and $CO_2$, organic acids, phenols, . . .

However, the acidity of a petroleum fluid, evaluated by its TAN, essentially depends on its carboxylic acid content, measured in the liquid fraction. Thus, the main function to be enriched by an isotope is the carboxylic acid function: RCOOH. The stable isotopes that can be used by the method according to the invention therefore have to be selected from among the isotopes of carbon, oxygen and hydrogen.

Labelling the carboxylic acid functions by oxygen 18 ($^{18}O$) by means of $CH_3^{18}OH$ for example, then using ratio $^{18}O/^{16}O$ can be mentioned by way of example. It is also possible to use the heavy isotope of hydrogen, deuterium, by means of $CD_3OH$, then the deuterium to hydrogen (D/H) ratio. However, different criteria have to be taken into account to obtain fast, accurate and inexpensive measurement:

the proportion and the cost of the reagent necessary for labelling, thus containing the stable isotope, have to be as low as possible, the ratio between the isotope used and the natural isotope has to be as high as possible, the reagent must be readily available (no long and complicated reactions, no rare or dangerous products, . . . ), the reaction allowing labelling of the acid functions must be easy to implement, the yield of the reaction allowing labelling of the acid functions must be satisfactory.

This is the reason why, according to an embodiment, one chooses to label the acid functions (and notably the carboxylic acid functions) by carbon 13 ($^{13}C$). In fact, $^{13}C$ is readily available and, above all, the $^{13}C/^{12}C$ ratio is 99.1%, which is remarkable for detecting very low enrichments in $^{13}C$. The reagent used can be, for example, an alcohol such as methanol or ethanol, diazomethane ($CH_2N_2$) or a halogenide. In the case of halogenides, the reaction allowing enrichment of the acid functions is written as follows:

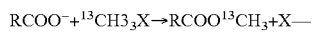

In the reagent $^{13}CH_3X$, halogen X can for example be chlorine ($CH_3Cl$), bromine ($CH_3Br$) or iodine ($CH_3I$). The most suitable and efficient one (in terms of volatility, reactivity and commercial availability) being iodomethane, the method will be described by means of this reagent without limiting the scope of the invention.

According to this embodiment, the method, simple to implement, then consists in converting in a weakly basic medium (in the presence of potassium carbonate $K_2CO_3$ to form the carboxylate ion $COO^-$) the carboxylic acid functions present in a petroleum sample into methyl esters by means of a carbon-13 labelled methylation reagent (equation 1):

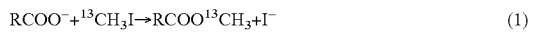 (1)

Whatever the nature of the sample (oil, extract, fraction, oil cut, . . . ), the labelling method remains the same as the method described hereafter within the context of crude oils. However, the preparation of certain types of sample will possibly require prior extraction and/or separation/distillation stages known to the man skilled in the art.

According to a first application example, the method is applied to a volume of crude oil. We add to 20 mg crude oil placed in a 5-ml drum 20 mg potassium carbonate $K_2CO_3$ (formation of salt COO—K+), 1 ml tetrahydrofurane THF (dissolution solvent), 1 ml methanol (aid to the dissolution of the potassium carbonate so as to form a homogeneous solution) and 50 μl $^{13}C$-labelled iodomethane (Cambridge Isotope Laboratories, 99%). The reaction medium is then placed under reflux with magnetic stirring, at 70° C., for 3 hours. After return to ambient temperature, the solvents and the excess iodomethane are evaporated in an argon stream for 15 minutes, then the reaction crude is subjected to ultrasonic extraction with dichloromethane (×3). The solution obtained is filtered on celite (placed in a funnel whose bottom is plugged by glass wool) and the solvents are again evaporated under reduced pressure. The reaction crude thus treated is diluted in dichloromethane so as to obtain a 20 mg·ml$^{-1}$ solution 10 μl of which are removed and placed in a tin boat or any sample holder required for further isotopic analysis. After evaporation of the solvent at ambient temperature, the boat is closed with a pinch cock and placed on the injection plate of the automatic sample changer of the elementary analyzer coupled with the isotopic mass spectrometer.

It can be noted that labelling according to this method can also affect other functions. In fact, the methylation reaction (equation 1) of the carboxylate ion is a nucleophilic substitution reaction. Consequently, any molecule having a (nucleophilic) free-electron doublet is likely to react according to this mechanism with the alkylating agent, such as phenols ($C_6H_5OH$), thiophenols ($C_6H_5SH$), amines ($RNH_2$) or thiols (RSH) for example. The specific feature of the isotopic carbon-13 labelling reaction towards carboxylic acids was verified. The tests carried out on model molecules and on oils rich in hetero-atoms (S, N, O) conclude that carboxylic acids are not the only species that can be labelled under the operating conditions used. Functionalized species like amines, azaarenes, phenols, thiols and sulfides can react with iodomethane, thus leading to the formation of labelled species and to an overestimation of the oil acidity via the $\Delta\delta^{13}C$ measurement. The higher the heteroelement content (S, N) of a crude, the more the $^{13}C$ incorporation rate will be affected without the oil having a high acid character. In this case, the $\Delta\delta^{13}C$-TAN correlation is no longer observed. However, our experimental conditions, which are relatively mild, limit the number of side reactions, thus preventing alkylation of the species whose pKa values are higher than those of potassium carbonate ($K_2CO_3$).

2—Measurement of the Isotopic Enrichment of the Oil Sample

After carbon 13 enrichment of the carboxylic acid functions, the isotopy of the carbon ($^{13}C/^{12}C$ ratio) of the initial sample and of the $^{13}C$-enriched sample is measured, then the isotopic enrichment linked with the incorporation of $^{13}C$ is determined. The isotopy of the carbon is measured by isotope ratio mass spectrometry (IRMS). Measurement of the isotopic enrichment being highly sensitive, it allows to measure a tiny $^{13}C$ enrichment, which is translated into a high increase in the $^{13}C/^{12}C$ ratio after labelling.

The isotopic measurements are performed by means of a Micromass Isoprime-EA type isotope ratio mass spectrometer using a NC 2500 Thermoquest type combustion oven and a Compaq Desktop EP series computer. The isotopic analysis conditions are as follows:

ionization energy: 100 eV combustion reactor temperature: 1030° C.

reduction reactor temperature: 650° C.

chromatographic column allowing these various gases to be separated helium flow rate: 100 ml/min.

3—Evaluation of the Oil Sample Acidity

On the one hand, the incorporation of $^{13}C$ is proportional to the amount of acid functions (essentially carboxylic) in the oil and, on the other hand, the $^{13}C$ enrichment is translated into an increase in the $^{13}C/^{12}C$ ratio. Thus, measurement of the isotopic enrichment, defined as the difference between the isotopic value of the carbon 13 of the initial oil (non-enriched)

and of the oil enriched in $^{13}C$, allows the acidity $A_h$ of the oil to be evaluated. We thus write the following formula:

$$A_h = \Delta\delta^{13}C = \delta^{13}C_e - \delta^{13}C_{ne}$$

with:
- $A_h$: oil acidity,
- $\Delta\delta^{13}C$: isotopic enrichment in carbon 13,
- $\delta^{13}C_e$: isotopic value of the carbon 13 in % of the enriched oil sample,
- $\delta^{13}C_{ne}$: isotopic value of the carbon 13 in % of the non-enriched oil sample.

And we have, for any sample:

$$\delta^{13}C_{sample}(\text{‰}) = \frac{R_{sample} - R_{PDB}}{R_{PDB}} \times 1000$$

with:
- R: ratio of the number of atoms of carbon 13 to the number of atoms of carbon 12: $R = {}^{13}C/{}^{12}C$,
- $R_{PDB}$: ratio R corresponding to an international standard referred to as "Pee Dee Belemnite".

$\Delta\delta^{13}C$ is thus proportional to the oil acidity and therefore provides a measurement of the acidity $A_h$ which is, as described below, proportional to the TAN value. This measurement is thus reliable and fast. Furthermore, it can be used on samples of any volume, even in very small amounts, typically below 20 mg. Other advantages and uses are described hereafter.

4—Uses of the Isotopic Measurement of the Acidity of an Oil Sample a) Correlation with the TAN Measurements The method according to the invention provides measurement of the acidity from isotopic labelling that can be directly correlated with the TAN values measured by means of the standard ASTM method D664. In fact, acidity measurements $A_h$ (from isotopic enrichment) on crude oils produced throughout the world show that, on the whole, there is a linear relation between isotopic enrichment and TAN values obtained according to the ASTM method D664 as illustrated in FIG. 1, which shows the acidity measured according to the method, from the isotopic enrichment $\Delta\delta^{13}C$ (in %), as a function of the TAN for these various crude oils.

Thus, during oil exploration and from core extracts, it is possible to estimate the acidity of the oil in place by conventional means, the TAN, and also, by means of the isotopic enrichment method, the acidity $A_h$. The TAN can then be estimated by means of a regression from the measurements of $A_h$. A $TAN_{equivalent}$ is then obtained. This allows to use the method according to the invention to provide an oil acidity value that can be directly compared with the TAN by means of the $TAN_{equivalent}$. According to the method, it is also possible to provide a chart allowing to directly obtain a TAN value from acidity measurement $A_h$. This chart is made by performing, on oil samples of different origins, TAN measurements and acidity measurements $A_h$ according to the invention.

Figure 3:
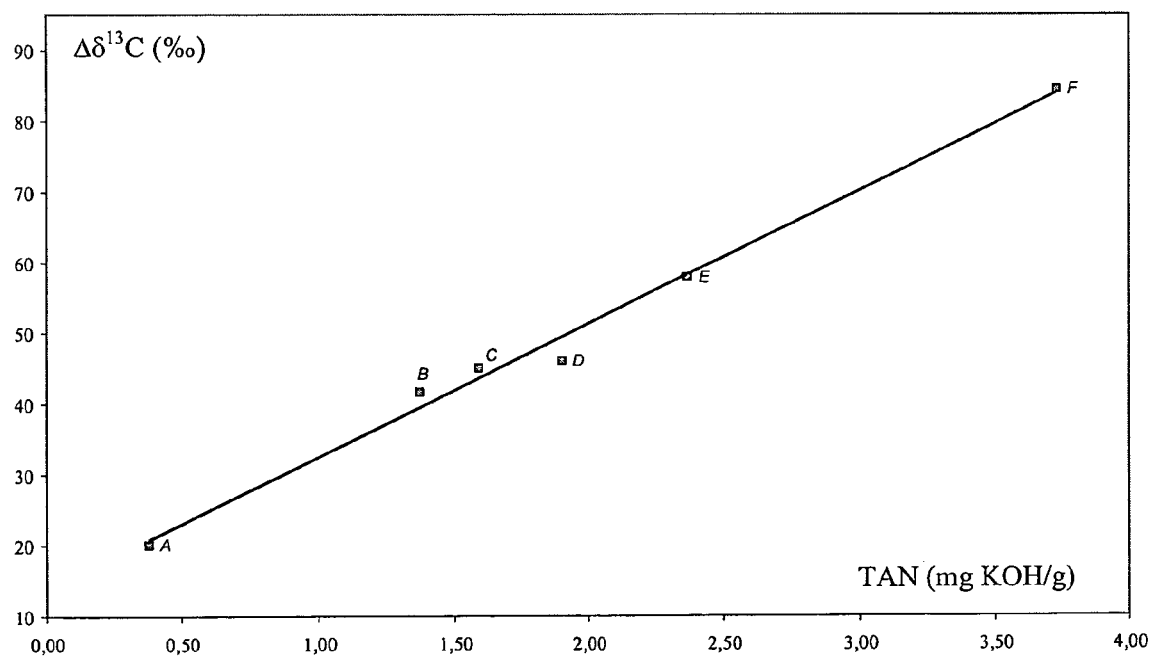
FIG. 3 illustrates the correlation between the TAN value (ASTM standard D664) and the $\Delta\delta^{13}C$ measurement of African oils of equal origin labelled with $^{13}C$.

This acidity determination method was applied to crude oils (A to F) of equal origin from an African field under production, having TAN values above 0.5 mg KOH/g oil (determined beforehand according to the standard ASTM method D664). FIG. 3 shows a perfect linear regression between the isotopic enrichment ($\Delta\delta^{13}C$ in %) and the TAN measurements for samples A to F of increasing biodegradation degrees.

b) Location and Characterization of the Molecules Responsible for Acidity

The acidity measuring method from an isotopic labelling only requires small amounts of samples (<20 mg). It therefore allows to study the acids of oil subfractions (chromatographic fractions for example). The method thus allows to locate and to characterize the molecules responsible for acidity in oils.

Oil or extract fractions/cuts are first obtained.

Oil or Extract Fractions

Oil or extract fractions of different polarity classes and/or different chemical families are obtained by thin-layer or liquid chromatography from the sample. The distribution in percent by weight of each one of these chemical families is thus obtained.

Oil or Extract Cuts

Oil or extract cuts are obtained by distillation. The carbon range of each cut is determined on the basis of the initial and final boiling point temperature of the cut under the distillation pressure conditions. The distribution in percent by weight of each one of the cuts is thus obtained.

The isotopic labelling protocol described above is then applied to about 20 mg of the various fractions/cuts obtained to determine the isotopic enrichment of each one and therefore to characterize the molecules responsible for acidity in the oils or the extracts. The acidity measurement obtained by means of the method is more accurate than with prior methods since measurement can be performed on sample fractions or cuts, and thus lead to locate the molecules responsible for acidity.

c) Aid to Technico-Economic Evaluation of an Oil Field

The production of acid oils involves many technical, economic and environmental problems. In fact, these biodegraded heavy crudes are characterized by a high acidity (TAN>0.5) and very high heavy metal, sulfur and nitrogen contents, in proportions that are much higher than those of conventional oils. These oils consequently require specific methods for production, transportation and treatment.

It is therefore very important to be able to define the acidity of an oil as early as possible during the development of an oil field. Now, evaluation of the TAN requires, as described above, large amounts of oil. On the other hand, the method according to the invention provides measurements on small amounts. Thus, at an early stage of production, although very small amounts of oil are available, it is possible to evaluate the acidity $A_h$. From this value and possibly by estimation of a TAN equivalent, $TAN_{equivalent}$, it is possible to rapidly know the optimum production, transportation and treatment conditions for the oil to be produced.

From the acidity measuring method according to the invention, it is possible to evaluate these optimum conditions. Rock samples such as cores, side wall cores, cuttings, . . . , are therefore used. The organic matter is then extracted from the organic matrix by means of a solvent extraction technique. Quantitative extraction of the organic matter contained in a crushed rock (from 1 g) is carried out with the dichloromethane used as extraction solvent and in a minimum proportion of 10 ml per rock range for 1 hour under reflux at 40° C. After returning to ambient temperature, the rock plus the extract are vacuum filtered. The extract collected in a drum is concentrated in an evaporator, then transferred in an aluminium boat to be weighed so as to obtain the amount of extract contained in the rock.

Figure 2:
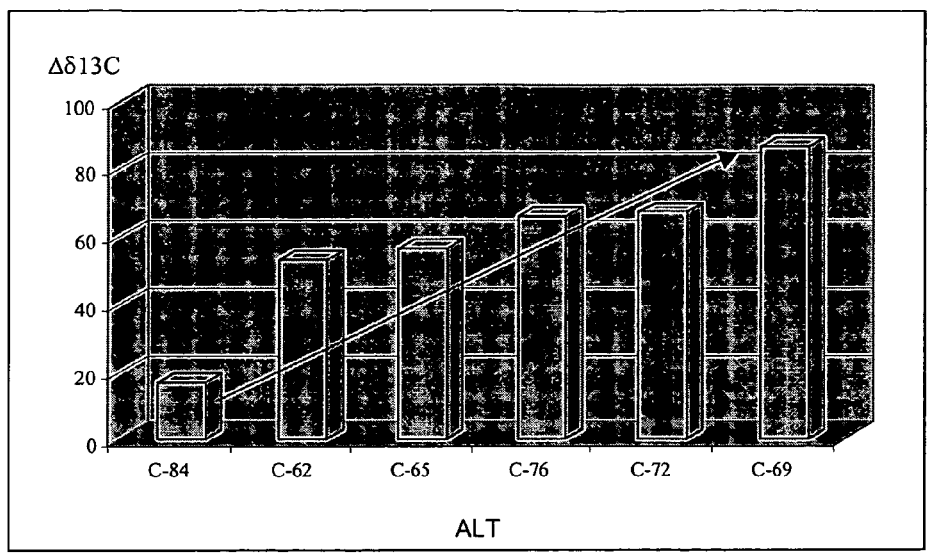
FIG. 2 shows the relation between the measurement performed $\Delta\delta^{13}C$ ($A_h$) and the alteration (ALT) by biodegradation obtained on core extracts from an oil field in Canada.

FIG. 2 shows the isotopic enrichment of carbon 13 ($\Delta\delta^{13}C$ in %) obtained for $C_{14+}$ extracts of Canadian cores altered at different biodegradation degrees (ALT) from the same field and from a single source. The isotopic labelling intensity is correlated with the core extract biodegradation intensity determined on the basis of the analysis of the elementary markers present in the various $C_{14+}$ extracts. The method according to the invention thus allows to determine the acidity of an oil from a field at an early development stage, thus allowing technico-economic evaluation of an oil field at an earlier stage than with a TAN measurement.

d) Evaluation of the Biodegradation of a Polluted Site

From the acidity measuring method according to the invention, it is possible to evaluate the evolution of the biodegradation of a polluted site. Rock samples such as cores are used. The organic matter is then extracted from the mineral matrix by means of a known extraction technique.

We can take up the example of FIG. 2 presenting the acidity obtained for $C_{14+}$ extracts of Canadian cores from the same field, altered at various biodegradation degrees. We see that the isotopic labelling intensity (or $A_h$) is correlated with the core extract biodegradation intensity determined on the basis of the analysis of the molecular markers present in the various $C_{14+}$ extracts.

It is thus also possible to monitor the evolution of the acidity (correlated with the isotopic enrichment) of a polluted site, the isotopic enrichment increase going together with the biodegradation intensity increase.

The advantages of the method then clearly appear:

the method intended for carbon 13 isotopic enrichment of drill cores allows, during oil exploration, to estimate the acidity of the oil in place, which can be directly correlated with the TAN values by calculating a TAN equivalent, acidity measurement according to the invention can be performed at a very early stage (before production), which allows a much more reliable technico-economic evaluation to be made. The means to be implemented for production, transportation and the refining methods can be optimized (selection of additives, catalysts, flexible sheaths, . . . ), acidity measurement according to the invention allows to readily monitor the evolution of the biodegradation of a polluted site from core samples for example, the prediction obtained according to the isotopic labelling method is more accurate since measurement can be performed on sample fractions or cuts, and can thus allow to locate the molecules responsible for acidity.

The invention claimed is:

1. A method for evaluating the acidity of an oil sample, characterized in that it comprises the following stages:
    carrying out isotopic enrichment of at least one acid function present in said sample,
    determining the value of said isotopic enrichment of said sample,
    deducing the acidity of said sample from said enrichment values.

2. A method as claimed in claim 1, wherein said isotopic enrichment is carried out from one of the following heavy isotopes: $^{13}C$, $^{18}O$, D.

3. A method as claimed in claim 2, wherein said isotope is carbon 13 ($^{13}C$).

4. A method as claimed in claim 3, wherein said enrichment comprises conversion of the carboxylic acid functions to methyl esters by means of a $^{13}C$-labelled methylation reagent.

5. A method as claimed in claim 1, wherein determination of the isotopic enrichment value comprises the following stages:
    measuring the isotopy of a chemical element of said sample prior to enrichment,
    measuring the isotopy of said chemical element of said sample after enrichment.

6. A method as claimed in claim 5, wherein said measurements are performed by isotope ratio mass spectrometry.

7. A method as claimed in claim 1, wherein the evolution of the biodegradation of a polluted site is evaluated from the following stages:
    extracting rock samples containing organic matter from said polluted site,
    extracting the organic matter,
    measuring acidity values $A_h$ of the organic matter from an isotopic enrichment,
    evaluating the evolution of the biodegradation of said polluted site from acidity $A_h$.

8. A method as claimed in claim 1, wherein production and transportation conditions for an oil from a field are optimized from the following stages:
    extracting rock samples containing organic matter from said field,
    extracting the organic matter,
    measuring acidity values $A_h$ of the organic matter from an isotopic enrichment,
    optimizing the oil production and transportation conditions from acidity $A_h$.

9. A method as claimed in claim 1, wherein molecules responsible for acidity are located and characterized by applying the following stages to oil extracts, subfractions or cuts:
    measuring acidity values $A_h$ of said oil extracts, subfractions or cuts from an isotopic enrichment,
    deducing from said acidity values $A_h$, for each oil extract, subfraction or cut, the location and the characterization of the molecules responsible for acidity.

10. A method as claimed in claim 9, wherein oil sample subfractions are obtained by thin-layer or liquid chromatography from the sample.

11. A method as claimed in claim 9, wherein oil sample cuts are obtained by distillation.

12. A method as claimed in claim 1 wherein a TAN value is estimated from the following stages:
    measuring TAN values of drill core extracts,
    measuring acidity values $A_h$ of said drill core extracts from an isotopic enrichment,
    determining a law allowing to relate said TAN values to said acidity values $A_h$,
    estimating a TAN value from said law and from all the acidity value measurements $A_h$ from an isotopic enrichment.

13. A method as claimed in claim 1, wherein a TAN value is estimated from a chart constructed from acidity values $A_h$ from an isotopic enrichment.

* * * * *